US00PP16825P2

(12) United States Plant Patent
Koeze

(10) Patent No.: US PP16,825 P2
(45) Date of Patent: Jul. 18, 2006

(54) ***BEGONIA* PLANT NAMED 'BBSOPHIA'**

(50) Latin Name: *Begonia×hiemalis*
Varietal Denomination: Bbsophia

(75) Inventor: Albertus Koeze, Aalsmeer (NL)

(73) Assignee: Begonia Breeders Assoc. B.V., Aalsmeer (NL)

( * ) Notice: Subject to any disclaimer, the term of this patent is extended or adjusted under 35 U.S.C. 154(b) by 12 days.

(21) Appl. No.: 11/097,673

(22) Filed: Mar. 31, 2005

(51) Int. Cl.
*A01H 5/00* (2006.01)

(52) U.S. Cl. ..... Plt./345
(58) Field of Classification Search ..... Plt./345, Plt./344
See application file for complete search history.

(56) References Cited

PUBLICATIONS

UPOV–ROM GTITM, Plant Variety Database, 2005/03, GTI Jouve Retrieval Software, Citation for Begonia 'Bbsophia'.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Begonia* plant named 'Bbsophia', characterized by its medium-sized, upright and mounded plant habit; double flowers with white-colored tepals; and excellent flower longevity.

1 Drawing Sheet

Botanical designation: *Begonia×hiemalis*.
Cultivar denomination: 'Bbsophia'.

BACKGROUND OF THE INVENTION

The present Invention relates to a new and distinct cultivar of *Begonia* plant, botanically known as *Begonia×hiemalis*, commercially known as Elatior *Begonia*, and hereinafter referred to by the name 'Bbsophia'.

The new *Begonia* was discovered and selected by the Inventor in a controlled environment in Aalsmeer, The Netherlands in April, 2002, as a naturally-occurring whole plant mutation of *Begonia×hiemalis* 'Dabra', not patented. The new *Begonia* was observed as a single plant in a group of flowering plants of the parent cultivar.

Asexual reproduction of the new *Begonia* by cuttings in a controlled environment in Aalsmeer, The Netherlands since 2002, has shown that the unique features of this new *Begonia* are stable and reproduced true to type in successive generations.

SUMMARY OF THE INVENTION

The cultivar 'Bbsophia' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bbsophia'. These characteristics in combination distinguish 'Bbsophia' as a new and distinct *Begonia:*

1. Medium-sized, upright and mounded plant habit.
2. Double flowers with white-colored tepals.
3. Excellent flower longevity.

Plants of the new *Begonia* can be compared to plants of the parent, the cultivar Dabra. Plants of the new *Begonia* differ primarily from plants of the cultiva Dabra in the following characteristics:

1. Plants of the new *Begonia* are more vigorous than plants of the cultiva Dabra.
2. Plants of the new *Begonia* and the cultivar Dabra differ in tepal color as plants of the cultivar Debra have yellow-colored tepals.

Plants of the new *Begonia* can also be compared to plants of the cultivar Clara, not patented. In side-by-side comparisons conducted in Aalsmeer, The Netherlands, plants of the new *Begonia* differed from plants of the cultivar Clara in the following characteristics:

1. Plants of the new *Begonia* had lighter green-colored leaves than plants of the cultivar Clara.
2. Plants of the new *Begonia* had less rounded flowers than plants of the cultivar Clara.
3. Plants of the new *Begonia* and the cultivar Clara differed in tepal coloration as plants of the cultivar Clara had green white-colored tepals.

BRIEF DESCRIPTION OF THE PHOTOGRAPH

The accompanying colored photograph illustrates the overall appearance of the new *Begonia*, showing the colors as true as it is reasonably possible to obtain in colored reproductions of this type. Colors in the photograph may differ slightly from the color values cited in the detailed botanical description which accurately describe the colors of the new *Begonia*. The photograph comprises a side perspective view of a typical flowering plant of 'Bbsophia'.

DETAILED BOTANICAL DESCRIPTION

In the following description, color references are made to The Royal Horticultural Society Colour Chart, 1995 Edition, except where geneal terms of ordinary dictionary significance are used. The aforementioned photograph and following observations and measurements describe plants grown in Aalsmeer, The Netherlands during the spring and summer, and grown under conditions typical of commercial practice in a glass-covered greenhouse. During the production of the plants, day and night temperatures ranged from 15 to 20° C. and light levels were about 18,000 lux. Plants used for the photograph and the description were grown in 13-cm containers and were about three months old when the photograph and description were taken.

Botanical classification: *Begonia×hiemalis* cultivar Bbsophia.

Commercial classification: Elatior *Begonia*.

Parentage: Naturally-occurring whole plant mutation of *Begonia×hiemalis* cultivar Dabra, not patented.

Propagation:

*Type.*—By cuttings.

*Time to initiate roots.*—About two weeks at temperatures of 20° C.

*Time to develop roots.*—About five weeks at temperatures of 20° C.

*Root description.*—Fine, fibrous and well-branched. Plants of the new *Begonia* have not been observed to form tubers.

Plant description:

*Plant form and habit.*—Medium-sized, upright and mounded plant habit; freely branching with about six to seven basal branches per plant. Moderately vigorous. Vegetative shoots are formed at basal nodes and flowering shoots are formed at upper nodes.

*Plant height.*—About 20 cm.

*Plant width.*—About 20 to 25 cm.

*Lateral branches.*—Length: About 9 to 14 cm. Diameter: About 1 to 3 cm. Texture: Smooth, glabrous. Color: 144B.

*Leaves.*—Arrangement: Alternate, simple. Length: About 7 to 8 cm. Width: About 6 to 7 cm. Shape: Roughly ovate; asymmetrical. Apex: Acute. Base: Oblique. Margin: Doubly crenate. Texture, upper and lower surfaces: Smooth, glabrous; velvety. Venation pattern: Palmate. Color: Developing and fully expanded leaves, upper surface: 136A. Developing and fully expanded leaves, lower surface: 139A. Venation, upper and lower surfaces: 136B. Petiole length: About 4 to 6 cm. Petiole diameter: About 4 mm. Petiole color, upper and lower surfaces: 136B. Stipule quantity: One to two per leaf. Stipule size: About 1 cm by 1 cm. Stipule texture, upper and lower surfaces: Smooth, glabrous. Stipule color, upper and lower surfaces: Close to 136A.

Flower description:

*Flowering habit.*—Double flowers with about 10 to 15 tepals per flower; flowers arranged in axillary cymes; about five to six open flowers per cyme; numerous cymes in flower simultaneously; about 30 to 42 open flowers per plant. Flowers positioned above and beyond the foliage and face upright to outwardly. Flowers not fragrant.

*Natural flowering season.*—Under natural daylight conditions, plants flower from spring until the fall. Flower initiation and development is induced by long day/short night conditions. Flowering continuous under photoinductive conditions.

*Flower longevity.*—Individual flowers last about four weeks on the plant; flowers persistent.

*Cyme height.*—About 4 to 5 cm.

*Cyme diameter.*—About 5 to 7 cm.

*Flowers.*—Shape: Oval to rounded; double. Diameter: About 4 to 5 cm. Depth (height): About 1 cm.

*Flower buds.*—Length: About 1 to 1.5 cm. Diameter: About 2 cm. Shape: Ovoid. Color: 155D.

*Tepals.*—Arrangement: Rosette. Shape: Obovate to rounded. Apex: Rounded to obtuse. Base: Obtuse. Margin: Entire. Length: About 2 to 3 cm. Width: About 3 to 4 cm. Texture, upper and lower surfaces: Smooth, glabrous; satiny. Color: When opening, upper and lower surfaces: 155D. Fully opened, upper surface: 155B; color becomes closer to 158D with development; margins of outer tepals occasionally tinged with close to 53A. Fully opened, lower surface: 155D; margins of outer tepals occasionally tinged with close to 53A.

*Flower bracts.*—Quantity: Two per flower. Arrangement: Opposite. Length: About 1 cm. Width: About 1 cm. Shape: Broadly cordate. Apex: Acute. Base: Cuneate. Margin: Entire. Texture, upper and lower surfaces: Smooth, glabrous. Color, upper and lower surfaces: 155D.

*Peduncles.*—Angle: About 30 to 45° from vertical. Length: About 4 to 5 cm. Diameter: About 3 to 4 mm. Strength: Strong. Texture: Smooth. Color: 145B.

*Pedicels.*—Angle: About 30 to 45° from vertical. Length: About 2 to 3 cm. Diameter: About 2 to 3 mm. Strength: Strong. Texture: Smooth. Color: 191D.

*Reproductive organs.*—Stamens: None observed. Pistils: None observed.

*Seed/fruit.*—Seed and fruit production has not been observed as reproductive organs are not formed.

Disease/pest resistance: Plants of the new *Begonia* have been observed to be resistant to Powdery Mildew. Plants of the new *Begonia* have not been observed to be resistant to pests and other pathogens common to *Begonia*.

It is claimed:

1. A new and distinct cultivar of *Begonia* plant named 'Bbsophia', as illustrated and described.

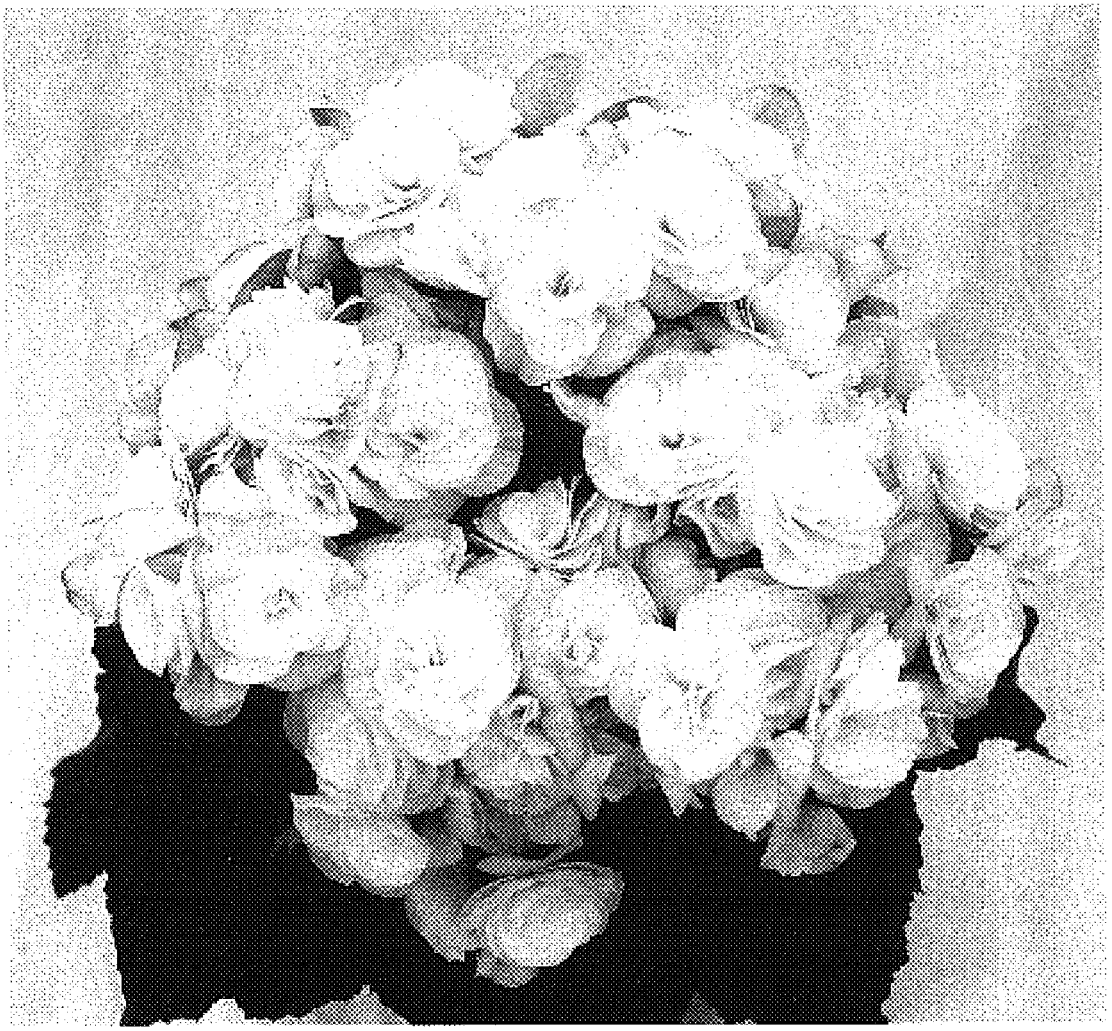

* * * * *